(12) United States Patent
Lippert-Gellissen et al.

(10) Patent No.: US 10,247,702 B2
(45) Date of Patent: Apr. 2, 2019

(54) BURNER NOZZLE

(71) Applicant: ABB SCHWEIZ AG, Baden (CH)

(72) Inventors: Julius Lippert-Gellissen, Hildesheim (DE); Matthias Graudenz, Bad Nauheim (DE); Paul Capek, Bad Soden am Taunus (DE); Peter Schastok, Niederdorfelden (DE); Stefan Filip, Haibach (DE)

(73) Assignee: ABB SCHWEIZ AG, Baden (CH)

( * ) Notice: Subject to any disclaimer, the term of this patent is extended or adjusted under 35 U.S.C. 154(b) by 0 days.

(21) Appl. No.: 15/842,909

(22) Filed: Dec. 15, 2017

(65) Prior Publication Data

US 2018/0106761 A1  Apr. 19, 2018

Related U.S. Application Data

(62) Division of application No. 15/371,237, filed on Dec. 7, 2016.

(30) Foreign Application Priority Data

Dec. 10, 2015  (DE) .......................... 10 2015 121 534

(51) Int. Cl.
*G01N 27/62* (2006.01)
*F23N 5/12* (2006.01)
(Continued)

(52) U.S. Cl.
CPC .......... *G01N 27/626* (2013.01); *F23D 14/58* (2013.01); *F23N 5/12* (2013.01); *F23D 2208/00* (2013.01);
(Continued)

(58) Field of Classification Search
CPC ...... G01N 27/62; G01N 27/626; G01N 30/68; F23D 14/58; F23D 14/68; F23N 5/12; Y10T 436/218
See application file for complete search history.

(56) References Cited

U.S. PATENT DOCUMENTS

| | | | |
|---|---|---|---|
| 6,715,432 B2* | 4/2004 | Tsumura | F23C 5/32 110/261 |
| 7,770,528 B2* | 8/2010 | Okazaki | F23D 1/00 110/264 |

(Continued)

FOREIGN PATENT DOCUMENTS

| | | |
|---|---|---|
| DE | 20320366 U1 | 7/2004 |
| JP | H 1038851 A | 2/1998 |

(Continued)

OTHER PUBLICATIONS

"Bunsenbrenner", Wikipedia, Die freie Enzyklopädie, pp. 1-2, Oct. 18, 2016.

*Primary Examiner* — Thang X Le
(74) *Attorney, Agent, or Firm* — Leydig, Voit & Mayer, Ltd.

(57) ABSTRACT

In an embodiment, the present invention provides a burner nozzle for a flame ionization detector, the nozzle including: an output-side outlet for ejecting a gas mixture to be ignited into a combustion chamber; an input-side inlet for feeding a combustible gas and a gaseous analyte through a transport channel to the outlet; and a cut-out, provided in the burner nozzle, through which cut-out combustion air can pass from the combustion chamber into the gas mixture flowing out of the outlet.

8 Claims, 1 Drawing Sheet

(51) Int. Cl.
*F23D 14/58* (2006.01)
*G01N 30/68* (2006.01)

(52) U.S. Cl.
CPC .......... *F23N 2029/12* (2013.01); *G01N 30/68* (2013.01); *Y02T 50/677* (2013.01)

(56) References Cited

U.S. PATENT DOCUMENTS

| | | | |
|---|---|---|---|
| 9,677,760 B2 * | 6/2017 | Hirano | F23C 6/045 |
| 2003/0146301 A1 * | 8/2003 | Sun | B05B 1/265 |
| | | | 239/399 |
| 2013/0333443 A1 * | 12/2013 | Miyai | G01N 27/626 |
| | | | 73/23.31 |
| 2015/0330956 A1 * | 11/2015 | Fogwill | G01N 30/68 |
| | | | 431/4 |
| 2016/0209032 A1 * | 7/2016 | Loveless | F23Q 9/00 |
| 2016/0245514 A1 * | 8/2016 | Ageno | F23L 15/02 |

FOREIGN PATENT DOCUMENTS

| | | | |
|---|---|---|---|
| JP | H 10206386 A | | 8/1998 |
| JP | 2000081205 | * | 3/2000 |
| JP | 2000081205 A | | 3/2000 |
| JP | 2008275569 A | | 11/2008 |

* cited by examiner

BURNER NOZZLE

CROSS-REFERENCE TO RELATED APPLICATIONS

This application is a divisional of U.S. patent application Ser. No. 15/371,237, filed on Dec. 7, 2016, which claims priority to German Patent Application No. DE 10 2015 121 534.9, filed on Dec. 10, 2015, the entire disclosures of which are hereby incorporated by reference herein.

FIELD

The invention relates to a flame ionization detector.

BACKGROUND

The field of application of the invention extends to process control systems in which organic compounds such as hydrocarbons in gases are measured and monitored, for example in the production of gases or the measurement of emissions from combustion of fossil fuels. In the commonly known prior art, flame ionization detectors (FIDs) are provided for this purpose, in which carbon-containing molecules in a gas flame are ionized and detected by measuring a current flow.

In order to generate a flame that is hot enough to ionize molecules, a hydrogen flame is needed. So-called combustion air provides the necessary oxygen. The hydrocarbons are admixed through the gaseous analyte to be measured and conveyed by a burner nozzle into a combustion chamber. The hydrogen combusts with the oxygen above the burner tip of the burner nozzle to form water. The hydrocarbons contained therein also combust and form carbon dioxide as well as water.

Inside the flame there is a zone having temperatures of from 1000 to 1500° C., in which ionized intermediates such as CHO+ ions are produced. These ions are drawn out of the flame by an applied electric field before they can completely convert into $CO_2$ and $H_2O$. The positively charged CHO+ ions are carried away via a cathode, thereby generating an electric current that is tapped via an amplifier.

In order to produce a CHO+ ion, an oxygen and a hydrogen atom must be present in the flame, which bond to a carbon atom. If the concentration of oxygen in the gaseous analyte increases, there will be more oxygen atoms available for the reaction, whereby the conversion rate of C—H bonds increases, whereas the amount of hydrocarbons remains the same. This oxygen cross-sensitivity is a well-known disadvantage of FIDs.

In order to reduce the problem of oxygen cross-sensitivity, the combustion air is passed into the combustion chamber separately from and before the combustible gas, instead of mixing said air with the combustible gas and gaseous analyte on the input side of the burner nozzle. The oxygen must then diffuse from the outside into the flame (diffusion flame).

Apart from cross-sensitivity, another fundamental problem is the substance-dependent sensitivity of the FID. The number of C—H bonds per molecule of the gaseous analyte increases the measured amperage. For example, methane, having four H-bonds per carbon atom, produces a higher probability of ionization than propane, which has a maximum of three H-bonds per carbon atom. The substance-dependent transformation ratio is one of the most important metrological characteristics of FIDs and is called a response factor.

DE 203 20 366 U1 discloses a FID in which a burner nozzle having two or more holes is used. This produces a plurality of flames that may, under the right circumstances, merge to form a large flame having an increased surface area. This allows more oxygen to diffuse into the flame, which is intended to reduce the oxygen error.

Fundamentally, the development and optimization of a FID is costly due to the multitude of influencing factors. Thus, although a FID as described here can be optimized to a very low oxygen error, this usually leads to other metrological characteristics deteriorating at the same time. The reason for this is that a low oxygen error in FIDs having a diffusion flame is achieved at low hydrogen and combustion air amounts or low combustion air pressure. This causes the flame to drop and widen, which causes the metal burner tip to heat up. The change in flame shape leads to a change in the response factor. The relevant response factor for methane thus rises sharply as soon as the flame becomes wider. When the flame drops to the level of the burner tip, the conversion rate of other hydrocarbons gets better and better, since the metal burner tip gets hotter and hotter. What appears to be a potential advantage quickly turns out to be a disadvantage, since the conversion rate, following a non-linear progression, very quickly becomes so large that this is overcompensated. On passing a threshold value, even small changes lead to a strong response factor change of over 30%. Because strict limits are set for the response factors when approving FIDs for stationary emission measuring devices as well as for exhaust gas measuring systems in the automotive industry, the permissible limit in each case would be exceeded as a result of response factor changes of more than 5 to 10%.

A further problem is that of thermally induced wear of the burner tip and electrode in the combustion chamber. Sensitivity is also lower in the presence of voluminous flames, since ions, which are created in the center of the flame, contribute comparatively less to the measured current flow when the flame gets bigger.

SUMMARY

In an embodiment, the present invention provides a burner nozzle for a flame ionization detector, the nozzle comprising: an output-side outlet configured to eject a gas mixture to be ignited into a combustion chamber; an input-side inlet configured to feed a combustible gas and a gaseous analyte through a transport channel to the outlet; and a cut-out, provided in the burner nozzle, through which cut-out combustion air can pass from the combustion chamber into the gas mixture flowing out of the outlet.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
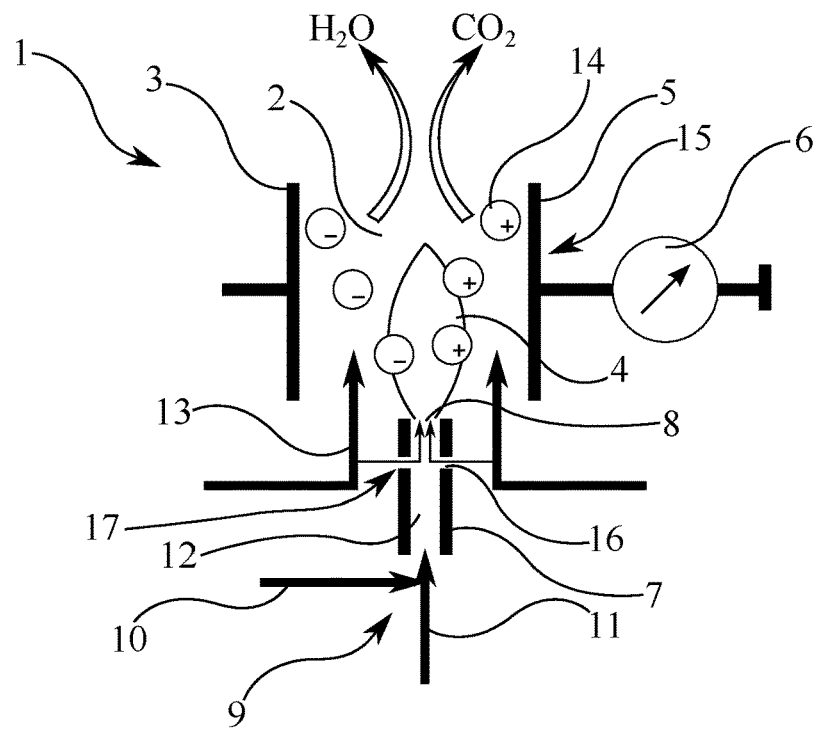
FIG. 1 is a diagram of a FID according to the invention comprising cut-outs in the form of holes.

An aspect of the present invention is to produce a FID in which the aforementioned problems relating to FIDs, such as cross-sensitivity and the influence of the response factor in particular, are reduced with as little complexity as possible.

An aspect of the invention relates to a flame ionization detector comprising a combustion chamber having an electrode arrangement for measuring an electric current of ions from a gas flame to an electrode of the electrode arrangement, to a burner nozzle having at least one output-side outlet for ejecting a gas mixture to be ignited between the electrode arrangement and having at least one input-side inlet for feeding a hydrogen-containing combustible gas and a carbon-containing gaseous analyte through a transport channel to the outlet, and to a means for feeding oxygen-containing combustion air into the combustion chamber. The invention also relates to an internal combustion engine, and to a power station and to a corresponding burner nozzle.

An aspect of the invention includes the technical teaching that at least one cut-out is provided in the burner nozzle, through which cut-out combustion air can diffuse from the combustion chamber into the gas mixture flowing out of the outlet.

In an aspect of the invention, the burner nozzle is therefore provided with a cut-out, for example a slot or an inlet hole. The cut-out is arranged such that some of the combustion air is fed into the combustible gas. This allows the combustion air to pass through the cut-out and into the gas mixture of combustible gas and gaseous analyte before reaching the flame, thus improving the oxygen supply to the flame.

This results in several advantages:

A reduction in the oxygen error can occur at significantly lower amounts of the combustible gas and combustion air. This causes the oxygen error to decline without negatively affecting the other metrological characteristics. Due to the lower amounts of the combustible gas and combustion air, the temperature in the combustion chamber decreases, thereby increasing the service life of the temperature-critical components. Additionally, less combustible gas and combustion air is used, which not only protects the environment but also expands the range of application of the FID and reduces its operating costs when using it for mobile exhaust gas measuring, for example in trucks and cars.

The temperature of the gas flame, and by extension that of the burner tip, also decreases as a result of the inflow of oxygen and nitrogen. Possible overcompensation of hydrocarbons having functional groups when the flame drops to the level of the burner tip, as is the case with other FIDs, is prevented. What can fundamentally be observed with this solution is that most response factors that are greater than 1 decrease, whereas others that are smaller than 1 increase slightly. For particular measurements, such as those carried out during waste incineration, this means that, when measuring unknown gas compositions, the sum of all hydrocarbons is closer to the actual concentration than is the case when using conventional FIDs.

The invention is improved by means of the burner nozzle comprising a conical burner tip, the outlet being arranged on the axis thereof.

In this case, the flame is spaced as far apart from the main body of the burner nozzle as possible; only the tip itself protrudes towards the flame. As a result, inter alia, thermally induced wear is minimized. It is also particularly easy to make a cut-out in a conical burner tip.

In a preferred embodiment of the invention, the at least one cut-out is designed to be a slot that is continuously open to the combustion chamber. It is therefore a gap that is laterally and continuously open to the flame. This allows for oxygen-containing combustion air to be laterally drawn in and to be mixed with the combustion gas/gaseous analyte mixture.

The advantage of this is apparent, inter alia, in effective transport of oxygen, since the dynamic negative pressure in the transport channel and above the outlet of the burner nozzle automatically sucks in surrounding combustion air. The simple manufacturing process is another advantage, since a conventional burner nozzle can be easily correspondingly reshaped, for example in the injection molding process or by means of subsequent machining.

This invention is further improved in that the slot extends over the outlet. This allows for particularly strong mixing of the combustion air and combustion gas/gaseous analyte mixture. Alternatively, the cut-out could also simply be arranged in the region surrounding the outlet without this being cut.

A preferred embodiment of the invention provides for the width of the slot to be equal to the diameter of the outlet. This makes mixing particularly effective: a narrower slot would let in comparatively little oxygen relative to the gas mixture, and a wider slot would cause the flame to drop as well as, inter alia, thermal damage to the burner tip.

A FID of this type is particularly preferable, the slot of which is delimited by walls that are arranged perpendicularly to one another. The cut-out thus has a rectangular profile comprising two side walls and a base surface. The outlet is optionally situated in the base. Alternatively, it would be possible, for example, to provide a cut-out having a V-shaped profile.

Another, likewise preferred embodiment is characterized in that the at least one cut-out is designed to be a hole in the burner nozzle. In contrast to the variant having the slot, the oxygen is in this case drawn in through at least one opening, for example in a side wall of the burner nozzle, and fed into the gas mixture. Advantageously, the outer surface of the burner tip, which is for example conical or cylindrical, remains largely undamaged in the process. A plurality of holes can also be provided, or one hole that ends in two openings in the burner nozzle.

It is particularly preferable in this instance that the hole comprises two openings into the combustion chamber and crosses the transport channel inside the burner nozzle so as to form at least two channels from the combustion chamber to the transport channel. A plurality of channel pairs of this type can also be provided, for example by means of holes through the transport channel that are at a different height or angle.

A FID 1 is shown schematically in FIG. 1, comprising a combustion chamber 2 in which an electrode arrangement 3 is arranged for measuring an electric current from a gas flame 4 to an electrode 5 of the electrode arrangement 3. The ammeter 6 comprises an amplifier (not shown in greater detail) in order to render measurable the typically very low currents from the gas flame 4.

A burner nozzle 7 protrudes into the combustion chamber 2 and comprises an output-side outlet 8 for ejecting a gas mixture 9 to be ignited between the electrode arrangement 3. The gas mixture 9 is formed on the input side of the burner nozzle 7 by a hydrogen-containing combustible gas 10 and a carbon-containing gaseous analyte 11 being mixed and guided through a transport channel 12 to the outlet 8.

Additionally, oxygen-containing combustion air 13 outside of the burner nozzle is conveyed into the combustion chamber 2. A reaction occurs with the combustible gas 10, whereby water ($H_2O$) and carbon dioxide ($CO_2$) are formed in the gas flame 4. Positively charged CHO+ ions 14 are also formed, which are accelerated by means of the electric field between the electrode arrangement 3 to the negatively charged cathode 15 and from there are conveyed away through the ammeter 6. The measured amperage then serves as the measure of the quantity of carbon dioxide in the gaseous analyte 11.

Two cut-outs 16 in the form of holes 17 are provided in the burner nozzle 7, through which some of the combustion air 13 can diffuse from the combustion chamber 3 into the gas mixture 9 flowing out of the outlet 8. The combustion air 13 is thereby incorporated into the gas mixture before reaching the gas flame 4. This ultimately reduces the oxygen cross-sensitivity of the FID without increasing the disruptive influence of the substance-specific response factor.

Figure 2:
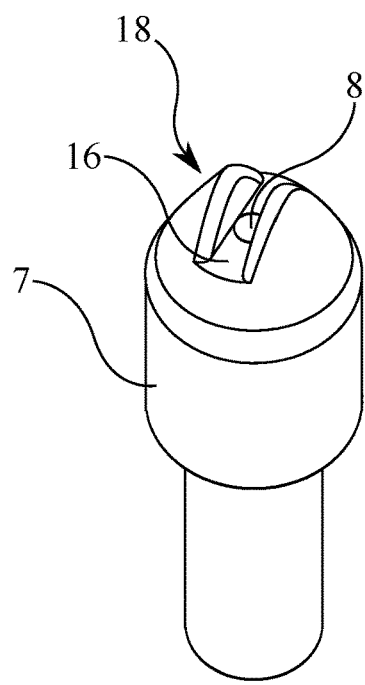
FIG. 2 shows a burner nozzle according to the invention comprising a cut-out in the form of a slot.

In accordance with FIG. 2, a burner nozzle 7 according to the invention comprises a conical main body having an outlet 8 arranged on the axis thereof. Additionally, and departing from the conical geometry, a cut-out 16 that is rectangular in profile is made in the burner nozzle 7 and is designed to be a slot 18 that is continuously open to the combustion chamber 3 (not shown in greater detail here), which slot extends over the outlet 8 and has a width that is equal to the diameter of the outlet 8. By means of this slot, the oxygen-containing combustion air 13 can laterally diffuse into the outflowing gas mixture 9 (not shown). As in the above-mentioned embodiment, combustion air 13 is thus incorporated into the gas mixture 9 in this way before reaching the gas flame 4 (not shown here). The lateral transport of the combustion air 13 does not have to be activated by means of specially provided actuators, but rather happens preferably automatically by means of the gas mixture flowing out of the outlet 8, facilitated for example by means of the Bernoulli effect.

The invention is not limited to the above-described embodiments. In fact, variants are also included therein which are contained within the following claims. It is therefore conceivable, for example, for the burner nozzle to be cylindrical instead of conical or for the slot to be V-shaped instead of rectangular.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B, and C" should be interpreted as one or more of a group of elements consisting of A, B, and C, and should not be interpreted as requiring at least one of each of the listed elements A, B, and C, regardless of whether A, B, and C are related as categories or otherwise. Moreover, the recitation of "A, B, and/or C" or "at least one of A, B, or C" should be interpreted as including any singular entity from the listed elements, e.g., A, any subset from the listed elements, e.g., A and B, or the entire list of elements A, B, and C.

LIST OF REFERENCE NUMERALS

1 Flame ionization detector
2 Combustion chamber
3 Electrode arrangement
4 Gas flame
5 Electrode
6 Ammeter
7 Burner nozzle
8 Outlet
9 Gas mixture
10 Combustible gas
11 Gaseous analyte
12 Transport channel
13 Combustion air
14 CHO+ ions
15 Cathode
16 Cut-out
17 Hole
18 Slot

The invention claimed is:

1. A burner nozzle for a flame ionization detector, the nozzle comprising:
   a transport channel;
   an output-side outlet on a first side of the transport channel, the output-side outlet being configured to eject a gas mixture to be ignited into a combustion chamber;
   an input-side inlet on a second side of the transport channel, the second side being opposite the first side, the input-side inlet being configured to feed a combustible gas and a gaseous analyte into the transport channel; and
   a cut-out provided in the transport channel that allows combustion air to pass from the combustion chamber, through the cut-out, and into the gas mixture present in the transport channel before the gas mixture is ejected from the output-side outlet.

2. The burner nozzle of claim 1, wherein the burner nozzle includes more than one of the cut-out.

3. The burner nozzle of claim 1, wherein the burner nozzle further includes a burner tip, on an axis of which burner tip the outlet is arranged.

4. The burner nozzle of claim 1, wherein the cut-out comprises a slot that is continuously open to the combustion chamber.

5. The burner nozzle of claim 4, wherein the slot extends over the outlet.

6. The burner nozzle of claim 5, wherein a width of the slot is equal to a diameter of the outlet.

7. The burner nozzle of claim 5, wherein the slot is delimited by one or more walls that are arranged perpendicularly to one another.

8. The burner nozzle of claim 1, wherein the cut-out comprises an inlet hole.

* * * * *